(12) United States Patent
Elliott et al.

(10) Patent No.: US 11,363,973 B2
(45) Date of Patent: Jun. 21, 2022

(54) NON-INVASIVE BLOOD ANALYSIS

(71) Applicant: LEMAN MICRO DEVICES SA, Lausanne (CH)

(72) Inventors: Christopher Elliott, St. Sulpice (CH); Mark-Eric Jones, Cossonay-Ville (CH)

(73) Assignee: LEMAN MICRO DEVICES SA, Lausanne (CH)

( * ) Notice: Subject to any disclaimer, the term of this patent is extended or adjusted under 35 U.S.C. 154(b) by 624 days.

(21) Appl. No.: 16/302,535

(22) PCT Filed: May 9, 2017

(86) PCT No.: PCT/GB2017/000068
§ 371 (c)(1),
(2) Date: Nov. 16, 2018

(87) PCT Pub. No.: WO2017/198981
PCT Pub. Date: Nov. 23, 2017

(65) Prior Publication Data
US 2019/0274601 A1 Sep. 12, 2019

(30) Foreign Application Priority Data
May 19, 2016 (GB) ..................................... 1608781

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1455* (2013.01); *A61B 5/14546* (2013.01);
(Continued)

(58) Field of Classification Search
CPC .............. A61B 5/1455; A61B 5/14532; A61B 5/14546; A61B 5/14552; A61B 5/6826
See application file for complete search history.

(56) References Cited

U.S. PATENT DOCUMENTS 4,882,492 A * 11/1989 Schlager ............ A61B 5/14532
600/322
5,099,842 A * 3/1992 Mannheimer ........ A61B 5/6834
600/323
(Continued)

FOREIGN PATENT DOCUMENTS

CN 201672970 U 12/2010
WO 2014125355 A1 8/2014

OTHER PUBLICATIONS

International Search Report and Written Opinion corresponding to PCT/GB2017/000068, dated Aug. 14, 2017, 25 pages.
(Continued)

*Primary Examiner* — Eric F Winakur
(74) *Attorney, Agent, or Firm* — J. Clinton Wimbish; Nexsen Pruet, PLLC

(57) ABSTRACT

A personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the processor of the PHHM is adapted to process the signals
(Continued)

received from the or each photo-detector to calculate the difference in intensity of light which has passed through the or each analyte cell and light which has passed through the or each non-analyte cell and to process signals obtained from the photosensor to provide a measurement of the concentration of the analyte in the user's blood, wherein either: •the or each photo-emitter is a light-emitting diode (LED); •an optical cell that mimics the absorption spectrum of the analyte to be detected is used and is a manufactured optical filter; •the PHHM is adapted to provide optical signals at one or more additional wavelengths for transmission to the body part, and the processor of the PHHM is adapted to process signals at the or each additional wavelength to estimate the volume of blood in the field of view of the blood photosensor; or •there is a ridge on the surface of the signal acquisition device between the photo-emitter(s) and the photo-detector(s).

14 Claims, 2 Drawing Sheets

(51) Int. Cl.
| | | |
|---|---|---|
| *G01N 21/47* | (2006.01) | |
| *G01N 21/49* | (2006.01) | |
| *A61B 5/024* | (2006.01) | |
| *G01N 21/31* | (2006.01) | |
| *A61B 5/02* | (2006.01) | |

(52) U.S. Cl.
CPC .......... *G01N 21/474* (2013.01); *G01N 21/49* (2013.01); *A61B 5/02007* (2013.01); *A61B 5/02438* (2013.01); *A61B 2560/0431* (2013.01); *G01N 21/31* (2013.01); *G01N 2021/3185* (2013.01); *G01N 2201/0221* (2013.01)

(56) References Cited

U.S. PATENT DOCUMENTS

| | | | |
|---|---|---|---|
| 5,167,230 A | 12/1992 | Chance | |
| 5,299,570 A | 4/1994 | Hatschek | |
| 5,348,003 A * | 9/1994 | Caro ................. | A61B 5/14546 600/310 |
| 5,424,545 A | 6/1995 | Block et al. | |
| 6,223,063 B1 * | 4/2001 | Chaiken ............. | A61B 5/14532 600/310 |
| 6,741,876 B1 * | 5/2004 | Scecina ............. | A61B 5/14532 600/316 |
| 7,418,284 B2 * | 8/2008 | DeLonzor .......... | A61B 5/14552 600/310 |
| 2005/0043597 A1 | 2/2005 | Xie | |
| 2006/0183983 A1 | 8/2006 | Acosta et al. | |

OTHER PUBLICATIONS

Timm, U et al., LED Based Sensor System for Non-Invasive Measurement of the Hemoglobin Concentration in Human Blood, IFMBE Proceedings 2008, vol. 23, pp. 825-828.

Danaei, Goodarz et al., National, regional, and global trends in fasting plasma glucose and diabetes prevalence since 1980: systematic analysis of health examination surveys and epidemiological studies with 370 country-years and 2.7 million participants, www.thelancet.com, Jul. 2, 2011, vol. 378, pp. 31-40.

World Health Organization, Global Status Report on Noncommunicable Diseases 2010, ISBN 978 92 4 156422 9, 164 pages.

Klonoff, Noninvasive Blood Glucose Monitoring, PubMed—NCBI, 2 pages.

Office Action dated Jul. 6, 2021, corresponding to Chinese application No. 201780030917.8, 17 pages.

Supplementary Search Report dated Jun. 29, 2021, corresponding to Chinese application No. 201780030917.8, 2 pages.

* cited by examiner

Alluxa OD6 Triple Band Emission Filter

NON-INVASIVE BLOOD ANALYSIS

CROSS REFERENCE TO PRIORITY APPLICATIONS

This application is a U.S. National Phase of PCT/GB2017/000068, filed May 9, 2017, which claims the benefit of Great Britain Application Number 1608781.9, filed May 19, 2016, each of which are incorporated herein by reference in their entireties.

FIELD OF THE INVENTION

The present invention relates to a personal hand-held monitor (PHHM) adapted to measure the concentration of an analyte in blood.

BACKGROUND TO THE INVENTION

There are many circumstances in which it is desirable to measure the concentration of an analyte in blood. One of the most important is the measurement of blood glucose concentration, of crucial importance to the management of diabetes. It is estimated by Danaei et al. ("National, regional, and global trends in fasting plasma glucose and diabetes prevalence since 1980: systematic analysis of health examination surveys and epidemiological studies with 370 country-years and 2.7 million participants", Lancet, 2011, 378(9785):31-40) that 370 million people in the world suffer from diabetes and the WHO predicts that diabetes will be the seventh leading cause of death by 2030 ("Global status report on non-communicable diseases 2010", WHO 2011). At present, the only accurate and inexpensive way for diabetics to measure their blood glucose concentration is by taking a blood sample, usually by pricking a finger, and placing a drop of blood on a test strip. A measurement of the change of colour of the strip or a measurement of a redox reaction on the strip after application of the blood sample provides an indication of the blood glucose concentration.

Inexpensive automated equipment exists to estimate the change in colour or the redox reaction but there is no consumer equipment capable of making the measurement without taking a blood sample and many diabetics have to do this several times per day.

Other analytes, such as alcohol, haemoglobin, creatinine, cholesterol, stimulants or other drugs, including illegal or otherwise forbidden substances, are also important and again there is no accurate, reliable and inexpensive way of estimating their concentration non-invasively.

In principle, absorption spectroscopy would be a good method for estimating the concentration of an analyte but this is difficult in vivo if the contribution to the absorption from the analyte is small compared to the absorption by other materials in the blood and tissue, especially if the analyte has few or no narrow absorption bands in the useable near infra-red (NIR) and/or if those bands are overlapping with those of water, which is the predominant component of blood and tissue. For example, Klonoff ("Non-invasive blood glucose monitoring", Diabetes Care, 20, 3, 435-437 1997) states: "Glucose is responsible for <0.1% of NIR absorbed by the body. Water, fat, skin, muscle and bone account for the vast majority of NIR absorption. Perturbations in the amounts of these substances can alter NIR absorption and thus invalidate the calibration formula for correlating light absorption with blood glucose concentrations . . . ".

Even if the problem of low absorption could be overcome, the measurement of the specific absorption would require a precise spectrometer that is not easily made inexpensively and reliably.

WO 2013/001265 discloses significant improvements on the prior art. Claim 25 of WO 2013/001265 relates a personal hand-held monitor (PHHM) comprising a signal acquisition device for acquiring signals which can be used to derive a measurement of a parameter related to the health of the user, the signal acquisition device being integrated with a personal hand-held computing device (PHHCD), wherein the signal acquisition device comprises a blood photosensor having a photo-emitter for transmitting light to a body part of a user, a photo-detector for detecting light transmitted through or scattered by the body part and an optical cell, containing an analyte to be detected, through which light transmitted through or scattered by the body part passes before it reaches the photo-detector, wherein the processor of the PHHM is adapted to process signals obtained from the photo-detector in the presence of the body part and in the absence of the body part to provide a measurement of the concentration of the analyte in the user's blood. WO 2013/001265 also discloses using the principle of two beams, one of which passes through a cell containing the analyte or mimicking the analyte, and comparing the power in each beam.

The invention disclosed in WO 2013/001265 goes some way towards the goal of a monitor that is non-invasive, inexpensive, accurate and reliable. However, it is not specific to the analyte contained in blood because the signal is also affected by analyte in the surrounding tissue. Further improvements are also desirable to reduce the cost of implementation and to improve accuracy.

WO 2014/125355 discloses a PHHM which has greatly improved performance compared to that of the PHHM of claim 25 of WO 2013/001265. It exploits more effectively a second degree of correlation to improve specificity. WO 2014/125355 teaches that the signal related to the concentration of the analyte may be correlated with the pulse, so as to make the signal preferentially sensitive to the change in the amount of analyte when the artery expands with each pulse. It further teaches that the change may be maximised by applying a pressure to the body part so as to cause the pressure around the artery to be similar to diastolic blood pressure. It further teaches that one of the optical cells may include a material that mimics the absorption spectrum of the analyte to be detected.

The PHHM of WO 2014/125355 represents a considerable advance on the prior art and allows accurate measurements to be made of the total amount of analyte in the field of view of the instrument. A further invention is needed to reduce the size and cost of the device and to improve the accuracy of the estimate of concentration. The size and cost of a product embodying the PHHM described in WO 2014/125355 is limited by the size and heat dissipation of the photo-emitter and the mechanical or other means of switching between the two beams. The accuracy is limited by the information available to normalise the measured signal to find the concentration of analyte from a measurement of the total quantity of analyte.

THE PRESENT INVENTION

According to a first aspect of the present invention, there is provided a PHHM of the type disclosed in WO 2014/

125355 wherein the or each photo-emitter is a light-emitting diode, as defined in appended claim 1. Preferred features are disclosed in claims 2 to 6.

The use of LEDs as the photo-emitters allows them to be brought closer to the body part.

The LEDs may be miniaturised and preferably are around 1 mm square.

Suitable LEDs are those manufactured by Epigap Optronic Gmbh. They are around 1 mm square and dissipate much less heat than thermal emitters. Epigap's standard products include:

| Part No | Centre wavelength | 50% bandwidth |
| --- | --- | --- |
| EOLC-1300-17-1 | 1300 | 85 |
| EOLC-1450-17-1 | 1450 | 100 |
| EOLC-1500-11 | 1550 | 120 |
| EOLC-1550-17-1 | 1550 | 130 |
| EOLC-1650-17-1 | 1650 | 100 |
| EOLC-1720-17-1 | 1720 | 100 |
| EOLC-1900-37 | 1920 | 100 |
| EOLC-2100-37 | 2100 | 150 |
| EOLC-2200-27 | 2200 | 150 |
| EOLC-2300-27 | 2300 | 150 |

The absorption spectra of glucose and blood are shown in FIG. 1. It is apparent that the wavelengths of the LEDs listed in the table above span several regions in which it is possible to differentiate glucose and blood. FIG. 2 shows part of the absorption spectrum of ethanol. Again, there is significant absorption, in this case at lower wavelengths than for glucose.

Preferably, not only the photo-emitter(s) but also the photo-detector(s) and the optical cell(s) are miniaturised. This eliminates the need for lenses, mirrors or fibre-optics.

According to a second aspect of the present invention, there is provided a PHHM of the type disclosed in WO 2014/125355 wherein an optical cell that mimics the absorption spectrum of the analyte to be detected is used and is a manufactured optical filter, as defined in claim 7.

Preferably, the filter takes the form of a glass sheet. The sheet is typically 1 to 2 mm thick.

FIG. 3 shows the transmission spectrum of a typical filter manufactured by Alluxa. It is possible to manufacture filters of this type with specific pass and stop bands. The pass and stop bands may be chosen to optimise the sensitivity of the measurements to the amount of analyte in the field of view, in accordance with the principles disclosed in WO 2014/125355.

WO 2014/125355 teaches that the signals indicative of the amount of analyte present may be normalised to estimate concentration using means for detecting the change in luminal area on each pulse. It teaches that such means may comprise optical sensors as described in WO 2013/001265.

According to a third aspect of the present invention, there is provided a PHHM of the type disclosed in WO 2014/125355 wherein the PHHM is adapted to provide optical signals at one or more additional wavelengths for transmission to the body part, and the processor of the PHHM is adapted to process signals at the or each additional wavelength to estimate the volume of blood in the field of view of the blood photosensor, as defined in appended claim 10.

For convenience, these will be called "secondary photo-emitters" and "secondary photo-detectors", to distinguish them from the primary components that detect the quantity of analyte. The optical sensors disclosed in WO 2014/125355 use two wavelengths of light (typically 640 nm and 950 nm) configured as the well-known pulse oximeter and optimized to estimate the ratio of oxygenated to non-oxygenated haemoglobin. Further information may be derived using additional wavelengths of light. For example, Timm et al in "*LED Based Sensor System for Non-Invasive Measurement of the Hemoglobin Concentration in Human Blood*" ICBME 2008, Proceedings 23, pp. 825-828, 2009 show that three additional wavelengths of 670 nm, 810 nm and 1300 nm allow the total haemoglobin also to be estimated.

According to a fourth aspect of the present invention, there is provided a PHHM of the type disclosed in WO 2014/125355 wherein there is a ridge on the surface of the signal acquisition device between the photo-emitter(s) and the photo-detector(s), as defined in appended claim 12.

A PHHM according to the present invention may comprise more than one or all aspects of the present invention in all of the possible combinations.

Preferably, the signal acquisition device of the PHHM of any of the aspects of the present invention is integrated with a personal hand-held computing device (PHHCD).

Preferably, in the PHHM of any of the aspects of the present invention:

the PHHM is adapted to apply pressure to the body part or to have pressure applied to it by the body part so that, in use, an artery in the body part changes from occluded to patent during each pulse;

the processor of the PHHM is adapted to determine the pulse of the user and to correlate the signals obtained from the photosensor with the pulse of the user; and the processor of the PHHM is adapted to derive a measurement of the change in the luminal area of the artery during each pulse and to correlate the signals received from the blood photosensor with the pulse and the change in the luminal area of the artery to provide a measurement of the concentration of the analyte in the arterial blood.

THE DRAWINGS

EMBODIMENT

An embodiment is described below with reference to the accompanying drawings. This embodiment shows how the aspects of the present invention may be combined, together with the principles set out in WO 2014/125355, to form a signal acquisition device that may be integrated with a PHHCD to create a PHHM for non-invasive blood analysis. The present invention is described below with reference to the accompanying drawing by way of example only. The invention is not limited to the embodiment shown in the accompanying drawing. The scope of the invention is defined in the accompanying claims.

Figure 4:
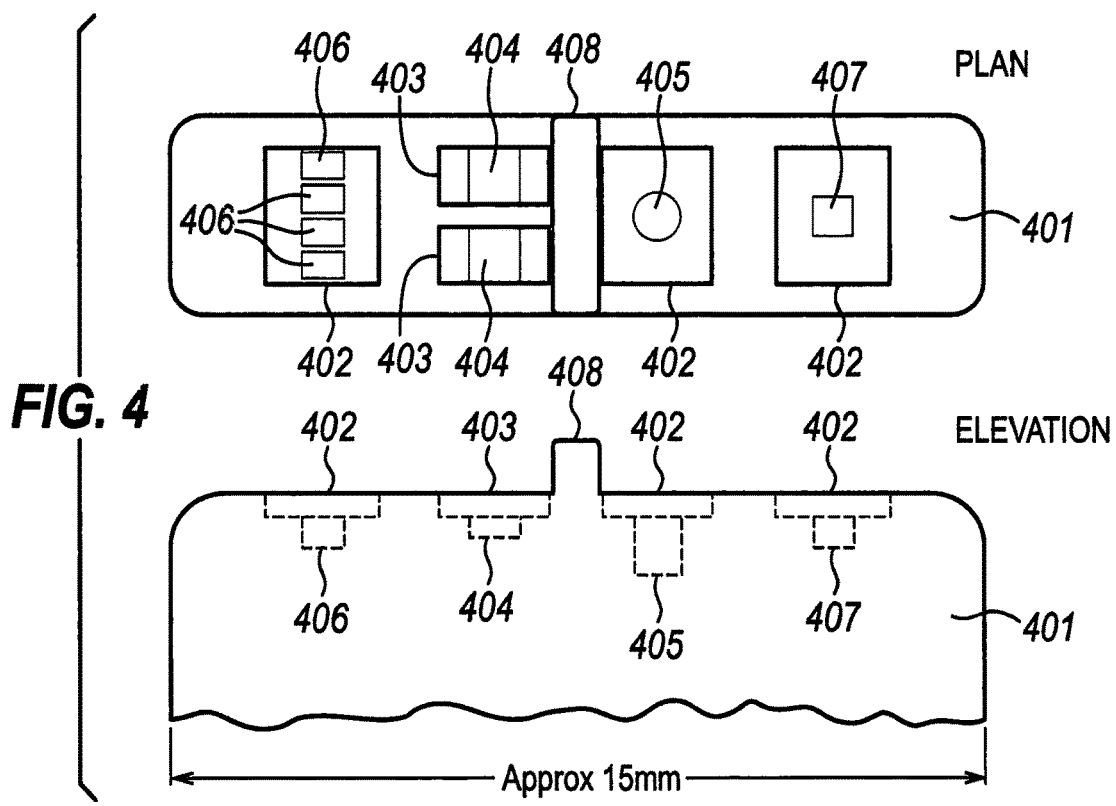
FIG. 4 shows an embodiment of the present invention.

FIG. 4 shows side elevation and plan views of the embodiment. This embodiment is suitable for carrying out measurement of an analyte in blood in, inter alia, the radial artery. There is a housing 401 that is approximately 15 mm long and 5 mm wide. The edges are rounded so that the housing may be pressed against the radial artery, causing occlusion when the pressure so created in the tissue exceeds diastolic blood pressure. The housing has three transparent windows 402 and a further split window 403, one half of which is an analyte cell in the form an optical filter. The other half is a non-analyte cell in the form of a transparent window or a further optical filter with different characteristics from the first optical filter.

There are provided two primary photo-emitter LEDs 404 and a single primary photo-detector 405. There are also provided four secondary photo-emitters 406 and a single secondary photo-detector 407. The various photo-emitters are switched to operate sequentially, as disclosed in WO 2014/125355, and the two photo-detectors 405 and 407 are used to measure the intensity of the light that has passed through or been scattered by the body part.

Alternatively, there may be two primary photo-detectors and one primary photo-emitter, where the two elements of the split window 403 are deployed in front of the two primary photo-detectors.

Figure 1:
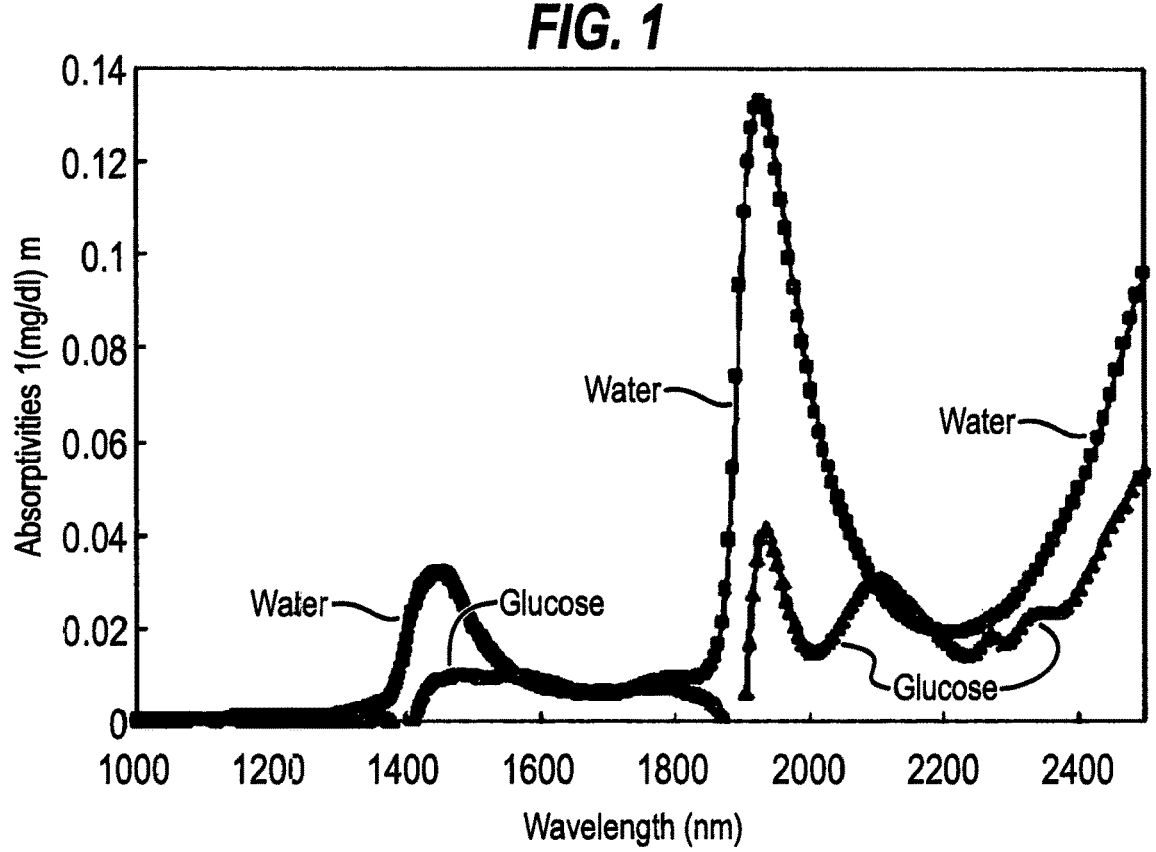
FIG. 1 shows the absorption spectra of glucose and water.
Figure 2:
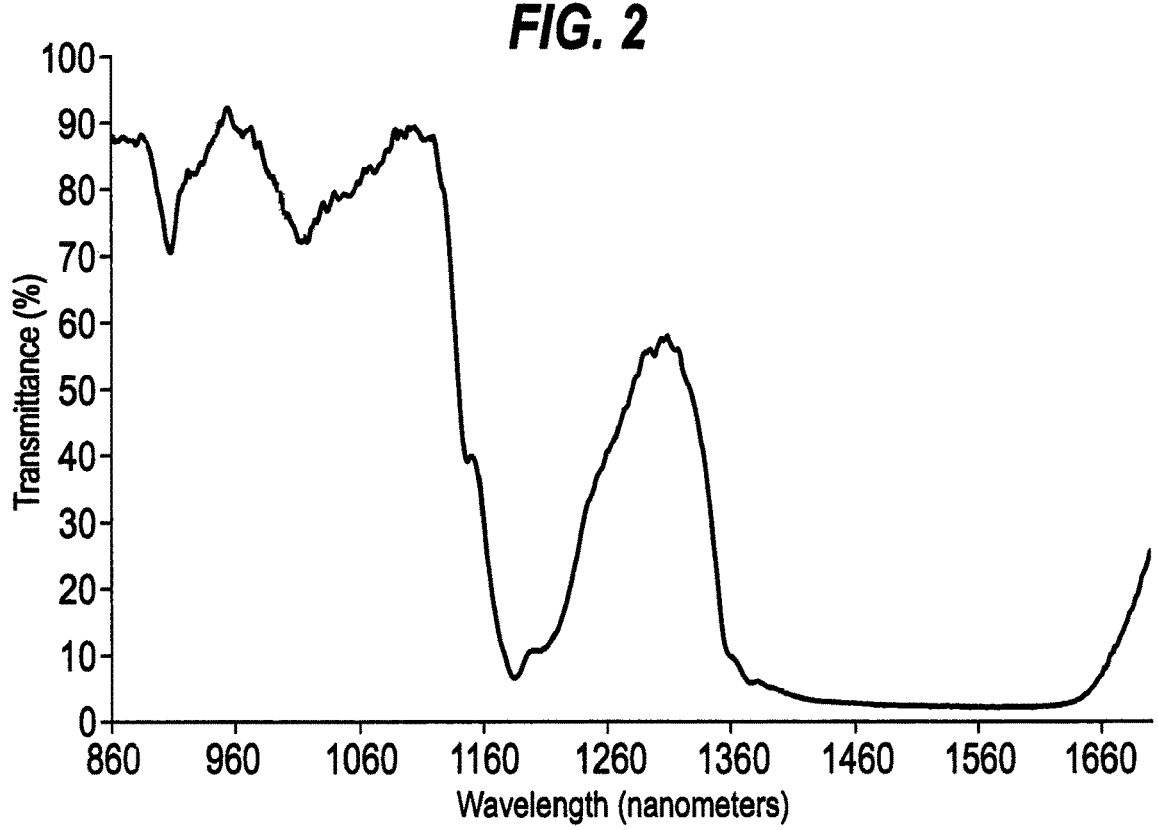
FIG. 2 shows part of the absorption spectrum of ethanol.
Figure 3:
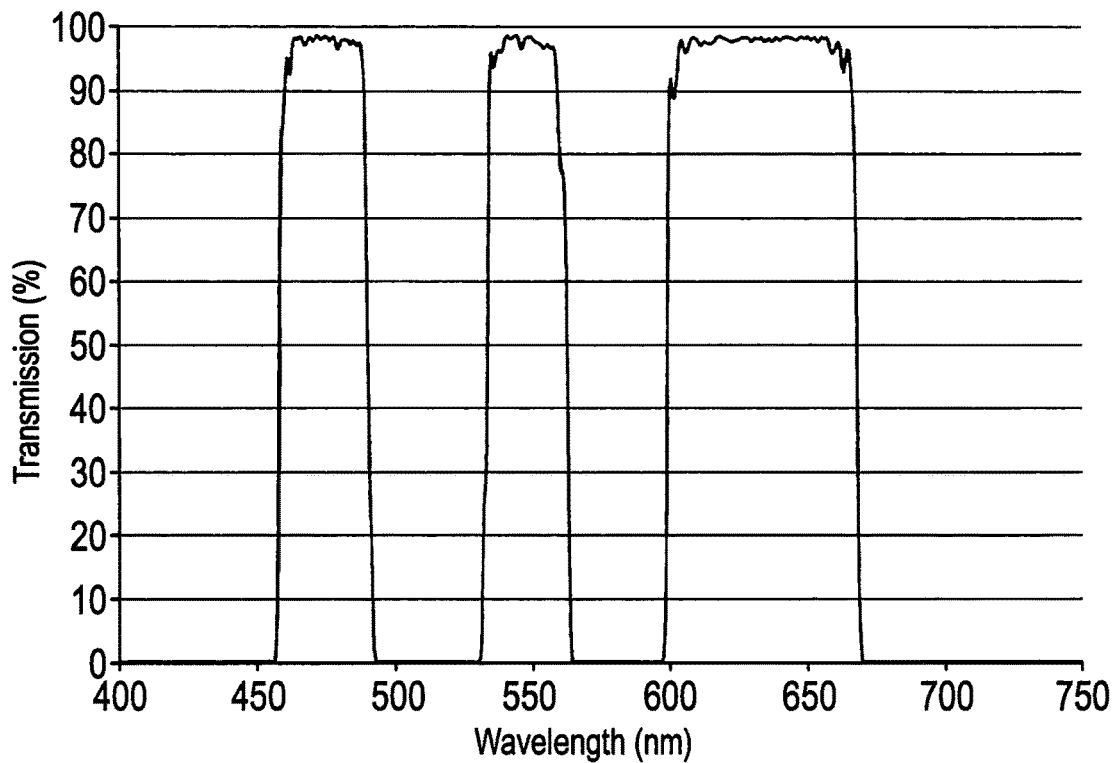
FIG. 3 shows the absorption spectrum of an example of a triple band emission filter.

Alternatively, the two primary photo-detectors or two primary photo-emitters may be located in the two beams of a beam splitter, as disclosed in FIG. 1 of WO 2014/125355. This is advantageous because it ensures that the same region of the body part is viewed by each photo-detector or illuminated by each photo-emitter.

The light propagated from the photo-emitter(s) reaches the photo-detector(s) by multiple scattering in the tissue of the body part. A ridge 408 approximately 1 to 2 mm high between them forces the detected signal to be derived from light that has travelled deeper into the body part than it could if the ridge were absent.

The invention claimed is:

1. A personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the PHHM comprises a processor adapted to process the signals received from the or each photo-detector to calculate the difference in intensity of light which has passed through the or each analyte cell and light which has passed through the or each non-analyte cell, wherein
the PHHM is adapted to apply pressure to the body part or to have pressure applied to it by the body part so that, in use, an artery in the body part changes from occluded to patent during each pulse;
the processor of the PHHM is adapted to determine the pulse of the user and to correlate the signals obtained from the photosensor with the pulse of the user;
the processor of the PHHM is adapted to derive a measurement of the change in the luminal area of the artery during each pulse and to correlate the signals received from the blood photosensor with the pulse and the change in the luminal area of the artery to provide a measurement of the concentration of the analyte in the arterial blood; and
the PHHM is adapted to provide optical signals at one or more additional wavelengths for transmission to the body part, and the processor of the PHHM is adapted to process signals at the or each additional wavelength to estimate the volume of blood in the field of view of the blood photosensor.

2. The PHHM of claim 1, wherein the additional wavelengths are chosen to optimize the estimation of haemoglobin content.

3. The PHHM of claim 1, wherein the signal acquisition device is integrated with a personal hand-held computing device (PHHCD).

4. The PHHM of claim 1, wherein the or each photo-emitter is a light-emitting diode (LED) having a 50% bandwidth of 85 nm or more.

5. The PHHM of claim 4, wherein the or each LED is around 1 mm square.

6. The PHHM of claim 1, wherein an optical cell that mimics the absorption spectrum of the analyte to be detected is used and is a manufactured optical filter.

7. The PHHM of claim 6, wherein the manufactured optical filter is a sheet of glass having a thickness of from 1 to 2 mm.

8. The PHHM of claim 6, wherein the manufactured optical filter is a sheet of glass.

9. The PHHM of claim 1, wherein there is a ridge on the surface of the signal acquisition device between the photo-emitter(s) and the photo-detector(s).

10. A personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the PHHM comprises a processor adapted to process the signals received from the or each photo-detector to calculate the difference in intensity of light which has passed through the or each analyte cell and light which has passed through the or each non-analyte cell, wherein
the PHHM is adapted to apply pressure to the body part or to have pressure applied to it by the body part so that, in use, an artery in the body part changes from occluded to patent during each pulse;
the processor of the PHHM is adapted to determine the pulse of the user and to correlate the signals obtained from the photosensor with the pulse of the user;
the processor of the PHHM is adapted to derive a measurement of the change in the luminal area of the artery during each pulse and to correlate the signals received from the blood photosensor with the pulse and the change in the luminal area of the artery to provide a measurement of the concentration of the analyte in the arterial blood; and
there is a ridge having a height 1 mm or more on the surface of the signal acquisition device between the photo-emitter(s) and the photo-detector(s).

11. The PHHM of claim 10, wherein the signal acquisition device is integrated with a personal hand-held computing device (PHHCD).

12. The PHHM of claim 10, wherein the or each photo-emitter is a light-emitting diode (LED) having a 50% bandwidth of 85 nm or more.

13. The PHHM of claim 10, wherein the PHHM is adapted to provide optical signals at one or more additional wavelengths for transmission to the body part, and the processor of the PHHM is adapted to process signals at the or each additional wavelength to estimate the volume of blood in the field of view of the blood photosensor.

14. The PHHM of claim 13, wherein the additional wavelengths are chosen to optimize the estimation of haemoglobin content.

\* \* \* \* \*